United States Patent [19]

Schwartz, deceased

[11] Plant 4,292

[45] Aug. 15, 1978

[54] ROSE PLANT

[75] Inventor: Ernest Schwartz, deceased, late of Kingsville, Md., by Hazel E. Schwartz, executrix

[73] Assignee: F. Harmon Saville Nor'East Miniature Roses, Rowley, Mass.

[21] Appl. No.: 854,511

[22] Filed: Nov. 25, 1977

[51] Int. Cl.[2] ..... A01H 5/00

[52] U.S. Cl. ..... Plt./7

[58] Field of Search ..... Plt./7

*Primary Examiner*—Robert E. Bagwill
*Attorney, Agent, or Firm*—Vincent G. Gioia

[57] ABSTRACT

A novel rose variety of the miniature rose class characterized by hybrid tea-like high centered blooms of orange-red to bronze-yellow coloring substantially as shown and described.

1 Drawing Figure

1

The present invention relates to a new and distinct variety of rose plant of the miniature rose class, which was originated by my crossing as seed parent the rose known as "Zorina" and an unnamed seedling as pollen parent.

Among the novel characteristics possessed by this new variety which distinguish it from its parents and all other varieties of which I am aware are: (1) strikingly colored blooms of unusually good high centered form borne primarily singly to a stem in a manner typical of hybrid tea plants, (2) flowers of good petalage displaying variable coloring under different lighting availability but featuring an orange-red to bronze blending with cream and yellow tones, and (3) a well branched, compact, upright growing plant. Asexual reproduction by budding of the new variety as performed in Essex County, Mass., shows that the foregoing and other distinguishing characteristics come true to form and are established and transmitted through succeeding propagations.

The new and improved rose variety which I have developed is an unusually fine miniature rose of orange-red to bronze blending singly-borne blooms of high centered, hybrid-tea like form are delightfully displayed on an upright growing compact plant. The flowers are unusually well formed, for a miniature rose and are of a novel coloring, varying under different light conditions, but generally producing an overall tonality reminiscent of a desert sunset coloring. The petals open sharply quilled forming star like points. The plant itself is attractive in combining medium, abundant foliage with well branching growth.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "40A" is plate 40A of the Royal Horticultural Society Color Chart.

Parentage: Seedling.
*Seed parent.*—"Zorina".
*Pollen parent.*—"Unnamed Seedling".

2

Class: Miniature.

The following observations are made of speciments grown outdoors in 30% shade in Essex County, Mass., during the month of October.

1. FLOWER

Blooming habit: Continuous.

A. Bud:
- (1) *Size.*—Medium.
- (2) *Form.*—Short, pointed.
- (3) *Color.*—When sepals first divide — 40A. When petals begin to unfurl — 14C flushed with 41B. When half-blown: 15A, edged with 41B. Reverse side of petals — 13C edged with 41C.
- (4) *Sepals.*—Extending slightly (about $\frac{1}{4}$-inch) beyond tip of bud (before opening), slightly foliated.
- (5) *Peduncle.*—Length — about 1-inch. Aspect — straight. Strength — erect, strong. Color — 143A.

B. Bloom:
- (1) *Size.*—Average size when fully expanded-about $1\frac{1}{2}$ inches.
- (2) *Borne.*—Primarily singly.
- (3) *Form.*—High centered blooms, becoming flat upon opening, petals quilling.
- (4) *Petalage.*—Number of petals under normal conditions — about 24 to 26.
- (5) *Color (during first 2 days).*—Inner petals at center of flower — 15C flushed with 41C. Outer petals — 15C flushed with 41C. Base of petals (point of attachment) — 10C. Reverse of petals — 14C flushed with 41D. General tonality from a distance — orange red-yellow blend.
- (6) *Color change.*—As bloom ages — yellow coloring becomes lighter and general tonality becomes bronze-yellow coloring, after 3 or more days color changes to 19D edged with 49A.

C. Petals:
- (1) *Texture.*—Medium.
- (2) *Appearance.*—Inside — satiny; Outside — satiny.
- (3) *Form.*—Sharply quilled forming star-like points.
- (4) *Arrangement.*—Imbricated.
- (5) *Petaloids in center.*—Few.
- (6) *Persistence.*—Drop off cleanly.

(7) *Fragrance.*—Sweet, strong for miniature.
(8) *Lasting quality.*—Average.

2. REPRODUCTIVE ORGANS

A. Stamens, filaments and anthers:
(1) *Arrangement.*—Regularly arranged.
(2) *Color.*—23A.
B. Pollen: Color — 23A.
C. Styles: Medium, uneven length.
D. Stigmas: Color — 49C.
E. Hips: None observed.

3. PLANT

A. Form: Upright, compact.
B. Growth: Vigorous, uniform branching. Height attained — 15 to 18 inches.
C. Foliage: Compound 5 to 7 leaflet leaves.
(1) *Size.*—Medium.
(2) *Quantity.*—Abundant.
(3) *Color.*—New foliage: Upper side — near to 137A. Under side — near to 138B. Old foliage: Upper side — 136B. Under side — 138C.
(4) *Shape.*—Pointed, oval.
(5) *Texture.*—Upper side — matte; under side — dull, veined.
(6) *Edge.*—Serrated.

(7) *Serration.*—Uniform.
(8) *Leaf stem.*—Color — near to 138B. Under side — 138B.
(9) *Stipules.*—Medium long, slightly bearded.
(10) *Resistance to disease.*—Blackspot — good. Mildew — good.
D. Wood:
(1) *New wood.*—Color — near 138A to 138B. Bark — smooth.
(2) *Old wood.*—Color — near to 138A to 138B. Bark — smooth.
E. Thorns:
(1) *Thorns.*—Quantity: very few, soft and thin. On laterals from stalk — very few. Form — long, thin, pointed, slanted downward. Length — medium. Color (when young) — 54C, older thorns 54B. Position — irregular.

I claim:

1. A new and distinct variety of rose plant of the miniature class, substantially as shown and described, characterized particularly by hybrid tea-like high centered, blooms of orange-red to bronze-yellow coloring borne primarily singly to a stem, deepening in tonality upon aging.

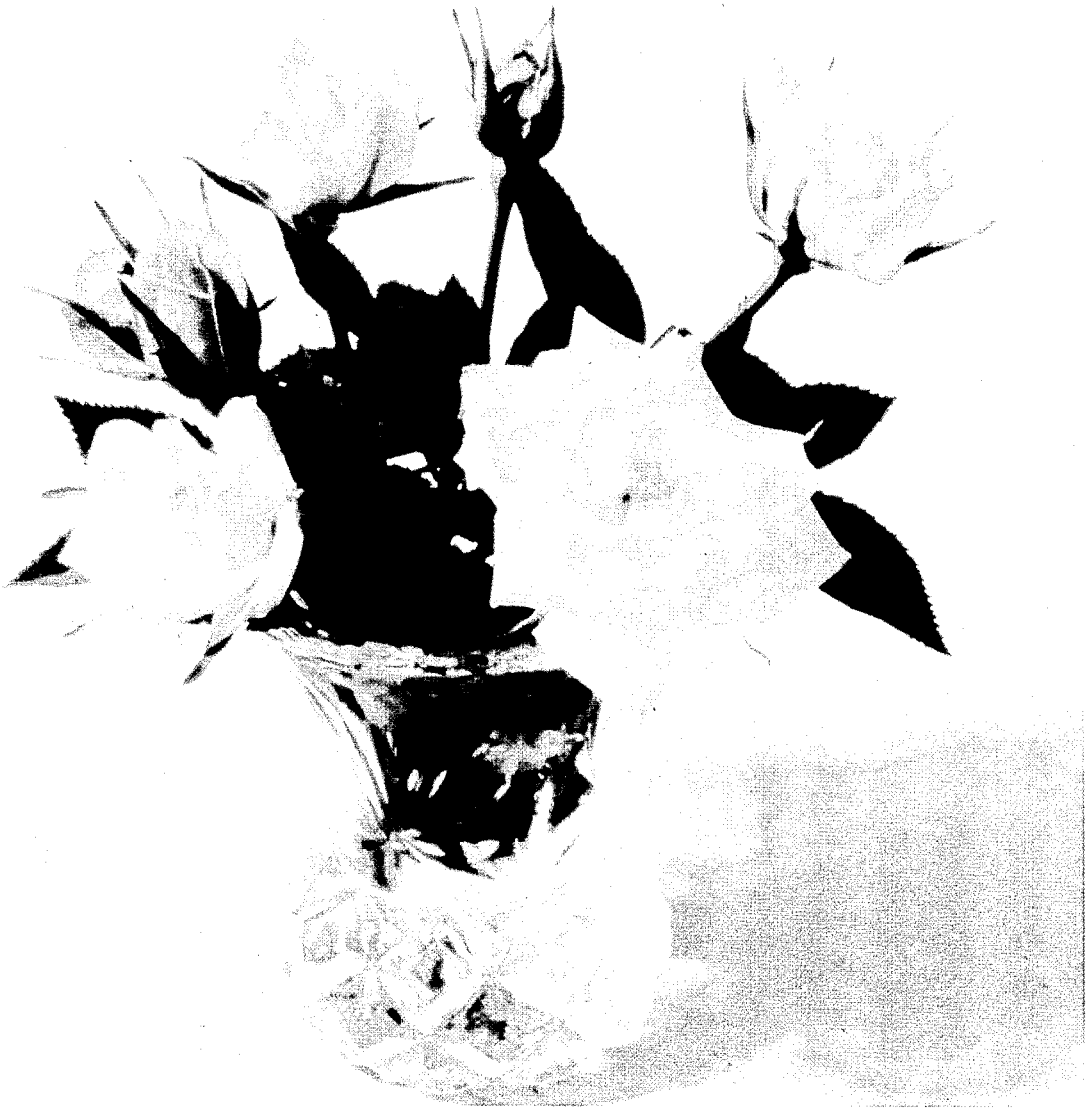

* * * * *